United States Patent [19]

Mahoney

[11] 4,155,713
[45] May 22, 1979

[54] ASSAY OF ANTIOXIDANT CONCENTRATION BY TITRATION WITH PEROXY RADICALS

[75] Inventor: Lee R. Mahoney, Livonia, Mich.

[73] Assignee: Ford Motor Company, Dearborn, Mich.

[21] Appl. No.: 846,246

[22] Filed: Oct. 27, 1977

[51] Int. Cl.$^2$ .......................................... G01N 33/28
[52] U.S. Cl. ............................ 23/230 HC; 23/230 M
[58] Field of Search .......... 23/230 R, 230 M, 230 HC

[56] References Cited

PUBLICATIONS

Salmonowicz et al.; "The Determination of Antioxidant Activity of Cocoa Hull Extract"; Zesz. Probl. Postepow Nauk Roln. 1973, No. 136, 215-219, (Eng.).
Hendrickson et al.; "Organic Chemistry—Third Edition"; McGraw-Hill Book Co.; 1970; pp. 826-827.

Primary Examiner—Arnold Turk
Attorney, Agent, or Firm—Edmund C. Ross, Jr.; Olin B. Johnson

[57] ABSTRACT

Effective antioxidant levels in hydrocarbonaceous materials are determined by (a) establishing the rate of uninhibited oxygen absorption for a standard liquid comprising (i) an oxidizable material susceptible to free radical oxidation and (ii) an agent that causes free radical oxidation; (b) establishing the rate of oxygen absorption for a test liquid comprising (a) (i) and (a) (ii) and a dispersible amount of the hydrocarbonaceous material or extract therefrom comprising antioxidant; (c) ascertaining the delay before uninhibited oxygen absorption of the test liquid and (d) determining the effective concentration of the antioxidant in the hydrocarbonaceous material. If the antioxidant in the hydrocarbonaceous material is known, the concentration can be accurately determined.

8 Claims, 3 Drawing Figures

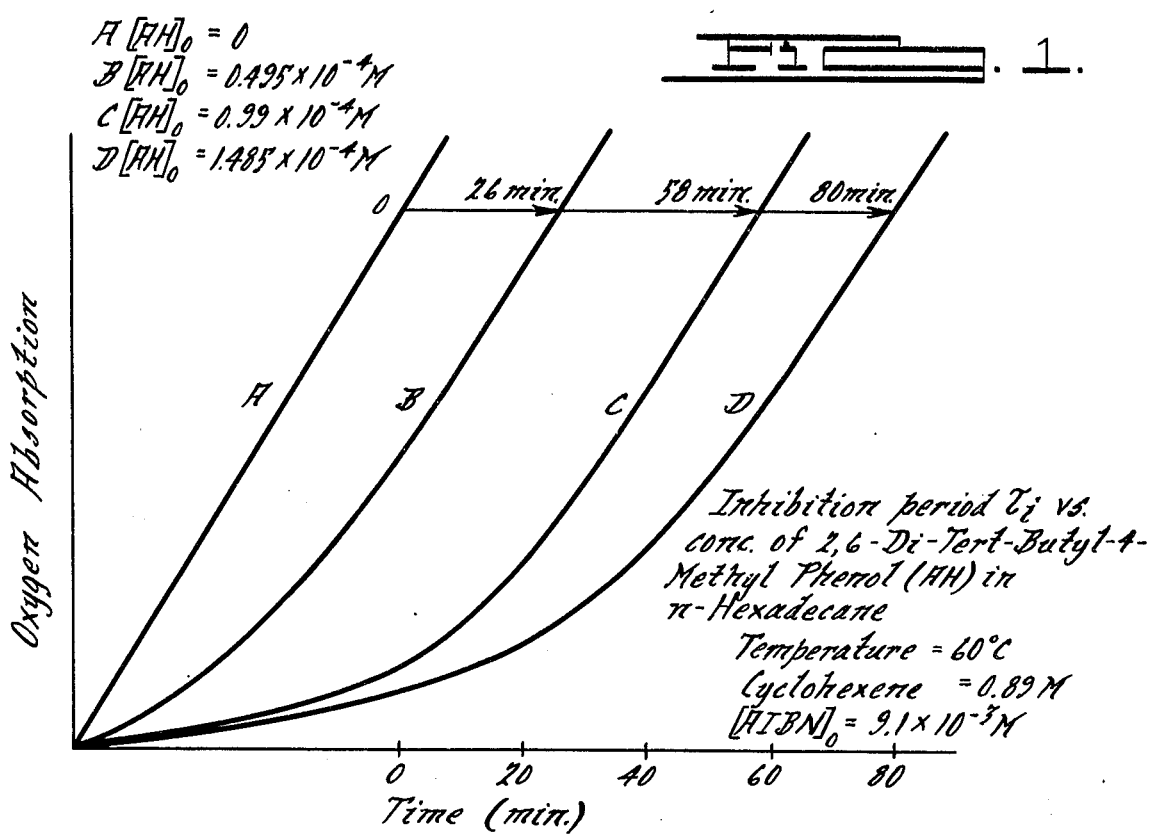
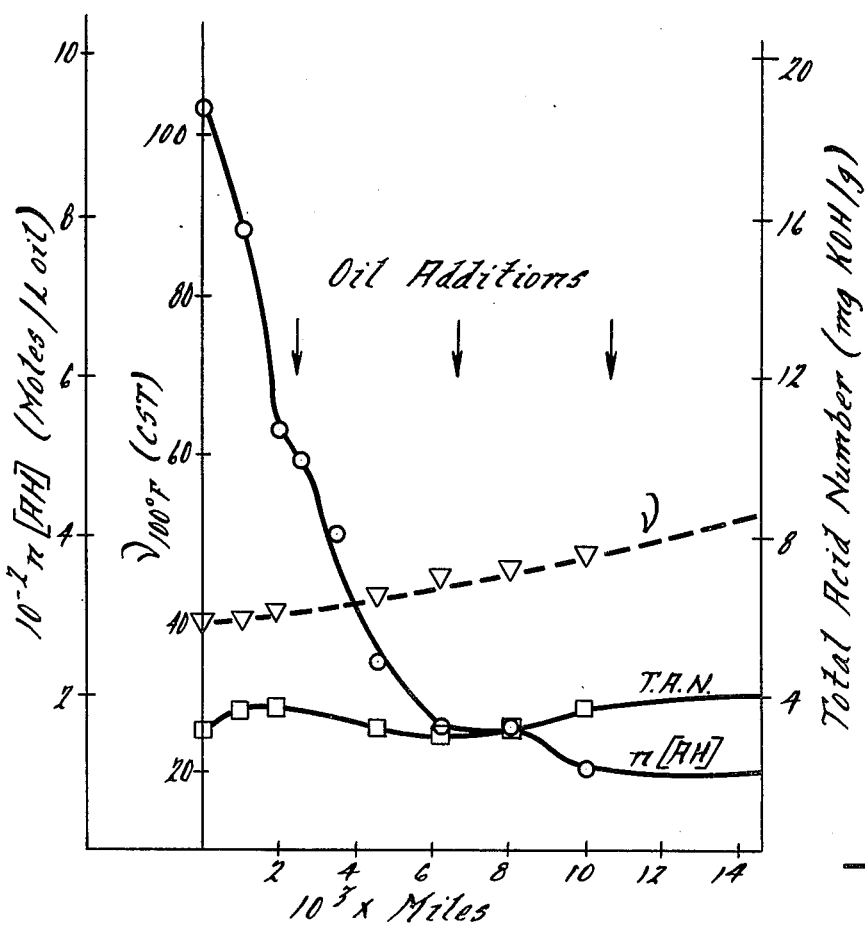

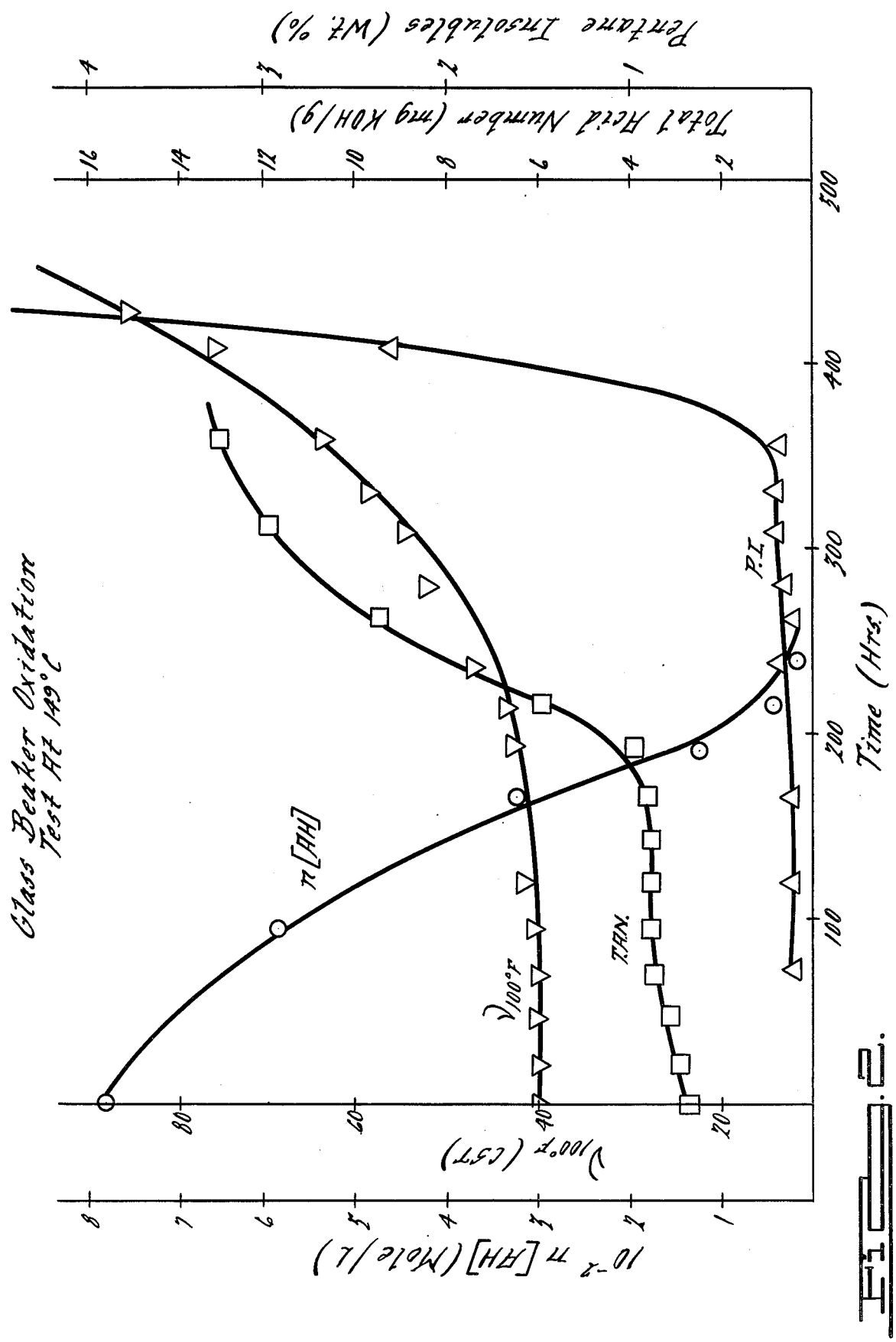

ASSAY OF ANTIOXIDANT CONCENTRATION BY TITRATION WITH PEROXY RADICALS

BACKGROUND OF THE INVENTION

This invention concerns a method for rapidly and accurately determining antioxidant levels in small samples of new and used hydrocarbonaceous materials by titration of antioxidant therein with peroxy radicals formed by agents that cause free radical oxidation acting on oxidizable substrates.

Routine analysis for antioxidant levels of food stuffs, fuels, lubricants, organic polymers and other hydrocarbonaceous materials is normally a difficult and tedious operation. Not only are the levels of antioxidants in hydrocarbonaceous materials very low, e.g., 1% by weight or less, but such antioxidants are also usually in complex admixture with other additives and/or decomposition products of the hydrocarbonaceous materials.

The method of this invention is specific for antioxidants which are free radical terminators and advantageously requires only very small samples for accurate determination of effective antioxidant levels.

Publications (disclosing methods) in which antioxidant levels are analyzed include: (1) "Determination of Diorgano Sulfide and Tertiary Phosphite Antioxidants in Polyolefins by Selective Oxidation with m-Chloroperoxybenzoic Acid" Kellum, Anal. Chem. 1971, 43(13), 1843-7, which discloses a step wise procedure for ascertaining levels of certain antioxidants, such step wise procedure not including measuring a rate of oxygen absorption; (2) "Determination of Antioxidant Activity of Cocoa Bean Shell Extract", Salmonowicz et al, Zesz Probl. Postepou Nauk Rolm., 1973, No. 136, 215-19 which discloses a comparative antioxidant analysis using thin-layer chromatography and comparative oxidation; (3) Hemoglobin Peroxidation Test Screens Antioxidants", Cost, Food Technol., 1974, 28(10), 60-6, which discloses use of oxygen absorption of aqueous emulsions; "Technique for Measuring Reactivity of Gasoline Antioxidants with Air" Strickland, Analytical Chemistry, 20, 55-56 (1948) which discloses an apparatus suitable for measuring oxygen absorption by systems comprising antioxidant; and "Possible Relation Between the Peroxide Number and Natural Antioxidants in Olive Oil" Incl. Agr., 6 (1), 21-24, 1968 which discloses iodometric method of analysis of antioxidant activity.

BRIEF DESCRIPTION OF THE DRAWINGS

FIG. 1 is a graph illustrating the oxygen absorption measurements obtained during use of the method of this invention when the nature and concentration of the antioxidant is known in the test solution.

FIG. 2 is a graph illustrating antioxidant concentration results of this invention according to the procedures of Example 1 wherein the antioxidant is unknown and the hydrocarbonaceous material is oxidized under laboratory conditions before testing in accordance with this invention.

FIG. 3 is a graph as in FIG. 2 wherein the hydrocarbonaceous material is aged under service conditions as set out in Example 3.

THE INVENTION

Basically, the method of this invention comprises (a) establishing the rate of uninhibited oxygen absorption for a standard liquid comprising (i) an oxidizable material susceptible to free radical oxidation and (ii) an agent that causes free radical oxidation; (b) establishing the rate of oxygen absorption for a test liquid comprising a(i) and a(ii) and a dispersible amount of the hydrocarbonaceous material or extract therefrom comprising antioxidant; (c) ascertaining the delay before uninhibited oxygen absorption of the test liquid; and (d) determining the effective concentration of the antioxidant in the hydrocarbonaceous material.

DETAILED DESCRIPTION OF THE INVENTION

This invention utilizes the principle that peroxy radicals generated in liquid systems can be used to, in effect, titrate antioxidant. The peroxy radicals are generated by reactions of agents that cause free radical oxidation and oxidizable materials susceptible to free radical oxidation in the presence of oxygen gas. When an antioxidant, which is a free radical terminator is introduced into such liquid system, the rate of oxygen absorption by the system is altered, i.e., inhibited, inasmuch as the antioxidant preferentially reacts with the peroxy radicals generated rather than the peroxy radicals acting on the further amounts of oxidizable material susceptible to free radical oxidation. (Further development of the type of reactions that may be involved can be obtained in the article Mahoney, L. R., *Ang., Chem., Int. Ed.,* 8, 546 (1969) which is herein incorporated by reference).

When the antioxidant is at a level such that it can no longer compete for the peroxy radicals generated, the rate of oxygen absorption of the liquid resumes its uninhibited rate. The delay before uninhibited absorption is proportional to the level of antioxidant in the system and independent of the nature of the antioxidant other than the number of peroxy radicals which react with each molecule of antioxidant. If the number of peroxy radicals which react with each molecule of antioxidant is known from other experiments, then an accurate determination of the actual concentration of antioxidant can be made. Otherwise, the effective antioxidant concentration can be accurately determined and this effective concentration is a small integer, e.g. 1, 2 or 3, times the actual concentration.

The rate of oxygen absorption is readily obtained for such systems by simply measuring the pressure of oxygen gas above the oxygen saturated liquid system as a function of time. A gas buret over a closed stirred liquid system can be utilized. A device such as that described in "Oxygen Absorption Apparatus", by L. R. Mahoney, inventor herein, in *Journal of American Chemical Society,* Vol. 86, p. 444, 1964, can also desirably be used. Basically, the device described therein uses a pressure transducer to read out the amount of oxygen absorbed by the oxygen saturated liquid system and such device can be used without modification in this invention for measurement of oxygen absorption.

Another way for establishing the rate of oxygen absorption is by measuring temperature change. As the oxygen is absorped by the system an exothermic reaction occurs. Upon consumption of antioxidant, the temperature increases at a different rate corresponding to the uninhibited rate of oxidation. The latter does need not to provide for constant temperature of the system but rather a thermistor contacting the system in such a way as to measure and record temperature change. For applications of thermal methods to determine oxidation rates (i.e. absorption of oxygen), see Reich, L. in *Macro-* molecular Reviews, Volume 3 (A. Peterlin et al), Wiley, Interscience, New York, 1968.

Agents that cause free radical oxidation which can be used herein are well known. They may be chemical agents as free radical initiators e.g. azobisisobutyronitrile or other agent that causes free radical oxidation of the oxidizable substrate. A list of chemical free radical initiators that cause free radical oxidation appears in Polymer Handbook, edited by J. Brandrup and E. H. Immergut; Interscience Publishers, J. Wilely and Sons, 1966, p. II–I et seq. Chemical free radical initiators are chosen so that they preferably have a convenient half-life of up to about 20 hours, more desirably up to about 12 hours, at between about room temperature and 100° C. Azobisisobutyronitrile is a preferred chemical agent for free radical oxidation. This is particularly so since it decomposes only to the extent of about 5 mole percent in about two hours, a convenient period to measure delay in oxygen inhibition. Moreover, it also is relatively insensitive to solvent effects thereby being particularly useful wherein added amounts of hydrocarbonaceous material are used. Other suitable free radical initiators will be apparent by reference to standard tests, or, if necessary, routine experimentation in accordance with the above criteria. Other agents for free radical oxidation include radiation energy as by ultraviolet light and electrochemical generation for free radical oxidation of oxidizable substrates.

The oxidizable materials in the liquid that are susceptible to free radical oxidation by the agent that causes free radical oxidation may be any organic compound which is more susceptable to free radical oxidation than the test hydrocarbonaceous material containing antioxidant. Desirably, the oxidizable material susceptable to free radical oxidation and the agent that causes free radical oxidation react to provide free radicals at a first order rate as measured by oxygen absorption. Aliphatic compounds including cycloaliphatic hydrocarbons as cyclohexene may be readily employed with suitable free radical initiators as azobisisobutyronitrile. Care should be taken, however, not to employ hydrocarbons such as alkylaromatic hydrocarbons as cumene which form hydroperoxides that rearrange into phenolic compounds that are themselves inhibitors. Such phenolic compounds acting as inhibitors will undesirably extend periods of inhibition giving too high a valve for antioxidant concentration.

Solvent or diluent is advantageously included in the liquid systems so as to facilitate contact of reactants as well as provide control of reaction rates. Polar and non-polar solvents and diluents may be used and straight chain alkanes of 12–20 carbons along with halogenated aromatics advantageously serve for analyzing a range of different hydrocarbonaceous materials. Other solvents and/or diluents may be selected as desired.

Important considerations in selection of solvent and diluent are (1) inertness under the conditions employed (2) an allowance of efficient rate of free radical production by the agent that causes free radical oxidation (3) a similarity to and compatibility with hydrocarbonaceous material to be tested particularly as to polarity, viscosity and stability.

Chlorobenzene and hexadecane are particularly preferred with the preferred free radical initiator AIBN in analyzing hydrocarbonaceous materials as lubricants. In these systems, the efficiency of free radical production at 60° C. is acceptably high (60% for chlorobenzene and 30% for hexadecane) and mixtures of these can be used to approximate a variety of viscosities of hydrocarbonaceous test material.

This invention may be better understood by reference to FIG. 1. In FIG. 1, the rate of oxygen absorption is plotted as a function of time for four solutions each of which comprises (i) cyclohexene, an oxidizable material susceptible to free radical oxidation, and (ii) azobisisobutyronitrile (AIBN), a free radical initiator dissolved in a hexadecane and chlorobenzene solution. Curve A shows the rate of oxygen absorption for a solution without an antioxidant which is a free radical terminator. This rate is the uninhibited rate of oxygen absorption. Curves B, C and D show the rate of oxygen absorption for solutions B, C and D, each of which also having varying amounts of antioxidant, 2, 6-di-tert-butyl-4-methylphenol (BHT). Solutions B, C and D have $0.495 \times 10-4$ moles, $0.99 \times 20-4$ moles and $1.485 \times 10-4$ moles of BHT, respectively, and, as can be seen, the delay before uninhibited oxygen absorption (as shown by comparing curves A, B, C and D) is directly related to the concentration of antioxidant in the system. As can also be seen, if solutions B, C and D were to contain an unknown level of antioxidant rather than a known amount, then the effective antioxidant level would become known from the plot of FIG. 1. Also, since from other experiments (see, for example, Hammond et al, *Journal of American Chemical Society* 77; 3233 (1955)) it is known that one mole of BHT terminates 2 moles of peroxy free radicals, then the delay before the rate of uninhibited oxygen absorption is twice as long as it would be if the antioxidant terminated only one mole of free radicals. Thus, Curve B, for example, would be the same for the liquid solution comprising twice as many moles of an antioxidant which terminates only one mole of free radicals.

The plot of FIG. 1 then can be used to determine by interpolation the effective concentrations in hydrocarbonaceous materials of unknown levels of known or unknown antioxidants by simply dissolving a portion of the hydrocarbonaceous material in the standard liquid and ascertaining the delay before uninhibited oxygen adsorption. After such delay is ascertained, the effective concentration can be determined from a comparison of such delay with the delays identified in FIG. 1. The results of this interpolation will yield the effective concentration of antioxidant.

Rather than plotting the delays in uninhibited absorption of oxygen, mathematical expressions can also be used to determine effective and actual concentration of antioxidants. It can be shown that when the delay before uninhibited oxidation is small and the half life of the chemical agent for free radical oxidation (e.g. AIBN) is large, the concentration in the system of antioxidant in moles times a constant is equal to a second constant times the inhibition period (i.e. period before uninhibited absorption of oxygen) times the initial concentration of free radical initiator in moles. The first constant is equal to the number of moles of peroxy radicals that react per mole of antioxidant and the second constant is the rate of free radical formation from the free radical initiator. Thus, by establishing the delay in uninhibited oxygen absorption at given conditions, the effective or actual concentration can be obtained by calculation.

As can be seen then, the antioxidant in the hydrocarbonaceous material or extract therefrom is titrated by peroxy radicals produced at a constant rate from a standard radical initiator acting on a hydrocarbon susceptible to free radical initiation, with the endpoint of the titration being the normal oxygen absorption of the system.

Advantageously, only very small amounts of hydrocarbonaceous materials are necessary in the method of this invention, e.g. a few grams or less, because of the accuracy of the titration; the total amount of antioxidant required for analysis is on the order of $10^{-7}$ moles. Thus, for antioxidant of molecular weight equal to 200 and at 1% by weight in the sample hydrocarbonaceous material only 2 milligrams of the sample is required for analyses. Moreover, the method can be used to obtain rapidly antioxidant levels. Thus, apparatus may be constructed which can in batch, or if desired, continuously monitor antioxidant levels in accordance with the method of this invention.

The following examples are intended to illustrate this invention but not be limiting thereof as many modifications of these examples will be apparent to those in the art.

EXAMPLE 1

In this example, the following test materials are used:

(1) Cyclohexene obtained from Eastman Organic Chemicals, distilled from calcium hydride (bp 83° C.) and passed through alumina immediately before use.

(2) n-Hexadecane (99+%) from Aldrich Chemical Company and passed through silica gel to remove polar impurities.

(3) Chlorobenzene from Baker Chemical Co., "Analyzed Reagent" grade, dried over anhydrous calcium sulfate and distilled through a short glass packed column; the fraction boiling at 132° C. collected and passed through alumina before use.

(4) Azo-bis-isobutyronitrile (AIBN) from Eastman Organic Chemicals, recrystallized twice from methanol and dried; mp 106–107° C.

(5) Silica gel used above for purificaftion obtained as Davison Grade 12 (28–200 mesh) purified by oxidizing organic impurities with hydrogen peroxide and multiple washings with water and methanol and then activated at 250° C. for 16 hours.

(6) Alumina obtained as Alcoa Type F-20 (80–200 mesh) from Matheson, Coleman and Bell and activated at 400° C. for 16 hours.

One ml. samples of a commercial engine oil aged by an accelerated laboratory oxidation test, comprising holding the test oil at a temperature of 149° C. with rapid stirring in the presence of air, diluted manyfold with n-hexadecane are employed. The experimental apparatus along with a general procedure can be found in Mahoney, L. R., *Journal of American Chemical Society;* 66, 444 (1964). A solution of 1 ml. oxidizable substrate (cyclohexene) in 9 ml. hydrocarbon solvent (hexadecane) is placed into the reaction cell. The reaction system is filled with oxygen and allowed to equiliberate at reaction temperature (60° C.) and pressure ≅750 mm. Hg. After equilibration 0.5 ml. of a solution containing the antioxidant in hexadecane (i.e. aged engine oil diluted with hexadecane) and 0.5 ml. of a solution of the thermal initiator (AIBN) in chlorobenzene (0.03–0.10 M) are injected into the reaction cell. At this point the measurement of oxygen absorption is initiated and continuously recorded as a function of time until the final uninhibited rate of absorption is achieved. The induction period is determined graphically as shown in FIG. 2. Also shown in FIG. 2 are results of values obtained using acid number, viscosity and pentane insolubles of the oil sample obtained by conventional techniques. It is to be noted that the onset of deterioration of the oil as measured by these latter techniques corresponds to nearly complete consumption of antioxidant according to the invention.

The oil is Mobil-1, a synthetic engine oil. The value n [AH] is the effective concentration of antioxidant. TAN is total acid number, $\gamma$ is viscosity at 100° F. and P.I. is pentane insolubles. The time on the x-axis is the time elapsed for a sample of oil at laboratory oxidation conditions described above.

EXAMPLE 2

In this example, the hexadecane, chlorobenzene, AIBN and cyclohexene are obtained and purified as in Example 1. A fully formulation rubber compound containing Flectrol H antioxidant is soaked in 7.0 ml. of chlorobenzene. Aliquots of the chlorobenzene soaking solution are removed at 1.5 hours soak, 14.2 hours soak and 127.0 hours soak and tested according to the general procedure of Example 1 to give the following concentrations of antioxidant (based on the independent measurement of one mole of Flectrol H antioxidant reacts with one mole of peroxy radicals generated by the AIBN system):

| Treatment Time | Concentration of Antioxidant |
|---|---|
| 1.5 hr. | $2.09 \times 10^{-2}$ m |
| 19.2 hr. | $4.13 \times 10^{-2}$ m |
| 127.0 hr. | $4.08 \times 10^{-2}$ m |

The amount of Flectrol H that is used in preparation of the rubber compound was $4.2 \times 10^{-2}$ m. Flectrol H is 1, 2-dihydro-2, 2, 4-trimethyl quinoline.

EXAMPLE 3

In this example, a commercial engine oil is tested in accordance with this invention wherein the oil is subject to actual operating conditions. New oil is added at about 3, 7 and 10 thousand miles to provide about a 20% by volume addition of oil.

The results of using the method herein in accordance with the procedures of Example 1 are shown in FIG. 3. For comparison the acid number and viscosity measurements are also shown. The value n[AH] is the effective concentration of antioxidant as measured by the procedure of Example 1. TAN is total acid number and $\gamma$ is viscosity at 100° F.

EXAMPLE 4

In this example, the effect of dilution of the hydrocarbonaceous material (commercially obtained engine oil) is analyzed at varying concentrations of AIBN in the test liquid. The engine oil is service derived. The procedures of Example 1 are followed to determine n[AH], i.e. effective antioxidant concentration.

As can be seen there is little or no effect due to dilution (Table 1, below). As also can be seen, the method herein is valuable since very low concentrations of antioxidant can be measured while possible interfering species are rendered less effective by dilution. Moreover, solvent effect by the hydrocarbonaceous material is minimized by its use at very low levels.

TABLE I

EFFECTS OF AIBN CONCENTRATION AND DILUTION ON VALUES OF n[AH] FOR A NEW AND USED ENGINE OIL

| Mileage on Oil | [AIBN] (M×10³) | DILUTION 1:X | 10²n[AH] (M) |
|---|---|---|---|
| 0 | 9.09 | 550 | 10.8 |
|  | 9.09 | 660 | 11.2 |
|  | 9.09 | 770 | 11.3 |
|  | 4.54 | 660 | 11.2 |
|  | 13.6 | 660 | 11.5 |
| 4,710 | 9.09 | 132 | 2.75 |
|  | 9.09 | 220 | 2.88 |
|  | 9.09 | 330 | 2.5 |
|  | 4.54 | 220 | 2.77 |
|  | 13.6 | 220 | 2.75 |

What is claimed is:

1. A method for measuring antioxidant levels in hydrocarbonaceous materials which comprises:
   (a) establishing the rate of uninhibited oxygen absorption for a standard liquid comprising (i) an oxidizable material more susceptible to free radial oxidation than a chosen hydrocarbonaceous material to be tested and (ii) an agent that causes free radical oxidation;
   (b) establishing the rate of oxygen absorption for a test liquid comprising (a)(i) and (a)(ii) and a dispersible amount of the hydrocarbonaceous material or extract therefrom containing the antioxidant;
   (c) ascertaining the delay before uninhibited oxygen absorption of the test liquid; and
   (d) determining the effective antioxidant concentration in the hydrocarbonaceous material.

2. The method in accordance with claim 1 wherein said oxidizable material susceptible to free radical oxidation comprises cyclohexene.

3. The method in accordance with claim 1 wherein said agent that causes free radical oxidation comprises azobisisobutyronitrile.

4. A method for measuring antioxidant levels in hydrocarbonaceous materials which comprises:
   (a) establishing the rate of oxygen absorption for a test liquid comprising (i) an oxidizable material more susceptible to free radical oxidation than a chosen hydrocarbonaceous material to be tested, (ii) an agent that causes free radical oxidation, and (iii) a dispersible amount of the hydrocarbonaceous material or extract therefrom containing the antioxidant;
   (b) ascertaining the time delay before uninhibited oxygen absorption of the test liquid; and
   (c) comparing the time before uninhibited oxygen absorption of the test liquid to the time before uninhibited oxygen absorption of a standard liquid containing (a) (i), (a) (ii) and a known amount of antioxidant to determine the effective antioxidant concentration in the hydrocarbonaceous material.

5. The method in accordance with claim 4, wherein the antioxidant comprises a phenolic antioxidant.

6. The method in accordance with claim 4, wherein the hydrocarbonaceous material comprises a lubricating oil.

7. The method in accordance with claim 6, wherein the agent for free radical initiation comprises a chemical agent having a half life up to 12 hours.

8. The method in accordance with claim 7, wherein the oxygen absorption is determined by sensing the temperature of the system.

* * * * *